(12) United States Patent
Chang et al.

(10) Patent No.: US 9,475,001 B2
(45) Date of Patent: Oct. 25, 2016

(54) EXTRACTING DEVICE SUPPLYING FIXED QUANTITY OF EXHAUST GAS FOR INDUSTRIAL FACILITY

(71) Applicant: KOREA DISTRICT HEATING CORP., Seongnam-si, Gyeonggi-do (KR)

(72) Inventors: Won-Seok Chang, Goyang-si (KR); Chang-Jun Lee, Suwon-si (KR); Jin-Bae Kim, Yongin-si (KR); Nam-Woong Kim, Seoul (KR)

(73) Assignee: KOREA DISTRICT HEATING CORP., Seongnam-si, Gyeonggi-do (KR)

( * ) Notice: Subject to any disclaimer, the term of this patent is extended or adjusted under 35 U.S.C. 154(b) by 169 days.

(21) Appl. No.: 14/333,392

(22) Filed: Jul. 16, 2014

(65) Prior Publication Data

US 2015/0192252 A1 Jul. 9, 2015

(30) Foreign Application Priority Data

Jan. 6, 2014 (KR) ........................ 10-2014-0001122

(51) Int. Cl.
| | |
|---|---|
| *B01D 53/84* | (2006.01) |
| *B01D 53/14* | (2006.01) |
| *F17D 3/01* | (2006.01) |
| *F17D 3/14* | (2006.01) |
| *F17D 5/00* | (2006.01) |

(52) U.S. Cl.
CPC ........... *B01D 53/84* (2013.01); *B01D 53/1475* (2013.01); *F17D 3/01* (2013.01); *F17D 3/14* (2013.01); *F17D 5/005* (2013.01); *Y02C 10/02* (2013.01); *Y10T 137/0396* (2015.04); *Y10T 137/3003* (2015.04); *Y10T 137/85986* (2015.04); *Y10T 137/86131* (2015.04); *Y10T 137/86163* (2015.04)

(58) Field of Classification Search
CPC ............ B01D 2257/504; B01D 53/84; B01D 53/1475; B01D 2251/95; Y02C 10/02; Y02C 20/152; Y10T 137/86163; Y10T 137/0396; Y02P 20/152
See application file for complete search history.

(56) References Cited

U.S. PATENT DOCUMENTS

| | | | |
|---|---|---|---|
| 2004/0008750 A1* | 1/2004 | Loncle | .................... C04B 35/83 374/16 |
| 2006/0240369 A1* | 10/2006 | Duesel, Jr. | ................ F23G 7/08 431/5 |
| 2008/0220486 A1* | 9/2008 | Weiss | ................... A61K 31/202 435/134 |
| 2010/0005722 A1* | 1/2010 | Iijima | ................ B01D 53/1412 48/128 |
| 2011/0107916 A1* | 5/2011 | Inoue | ................. B01D 53/1418 96/242 |
| 2012/0141352 A1* | 6/2012 | Lang | ...................... B01D 53/24 423/421 |
| 2014/0366721 A1* | 12/2014 | Roy | ..................... B01D 46/444 95/22 |
| 2015/0047366 A1* | 2/2015 | Carroni | ................. F01K 23/101 60/779 |

FOREIGN PATENT DOCUMENTS

KR          10-1072844 B1    10/2011

* cited by examiner

*Primary Examiner* — Atif Chaudry
(74) *Attorney, Agent, or Firm* — Novick, Kim & Lee, PLLC; Jae Youn Kim

(57) ABSTRACT

The present invention relates to an extracting device supplying fixed quantity of exhaust gas for industrial facility, and more particularly, to an extracting device supplying fixed quantity of exhaust gas for industrial facility which supplies a certain amount of exhaust gas by installing a gas supply pipe, in which two blowers are arranged in a line, at a stack and operating each blower in accordance with a predetermined input value.

9 Claims, 2 Drawing Sheets

EXTRACTING DEVICE SUPPLYING FIXED QUANTITY OF EXHAUST GAS FOR INDUSTRIAL FACILITY

TECHNICAL FIELD

The present invention relates to an extracting device supplying fixed quantity of exhaust gas for industrial facility, and more particularly, to an extracting device supplying fixed quantity of exhaust gas for industrial facility which supplies a certain amount of exhaust gas by installing a gas supply pipe, in which two blowers are arranged in a line, at a stack and operating each blower in accordance with a predetermined input value.

BACKGROUND ART

Due to emission of greenhouse gas caused by the use of fossil fuels, global warming has resulted in changes in climate and global environment, thereby threatening the survival of all living things on earth including human beings. Accordingly, various researches and developments for reducing carbon dioxide are now in progress. As one of efforts, study on the way of capturing and biologically converting carbon dioxide is actively underway.

As a green plant which performs photosynthesis for biologically converting carbon dioxide, microalgae have been actively studied. In common with other green plants in photosynthetic process, microalgae, phytoplankton, use sun as an energy source and grow up with photosynthesis for biofixation of carbon dioxide.

The first reason for recognizing microalgae as a means of biofixation of carbon dioxide is very low amount of energy to be injected for capturing carbon dioxide, because solar energy may be the main energy source as the same with absorption of carbon dioxide. Thus, since there is less amount of generating carbon dioxide for operation of biofixation of carbon dioxide, removal efficiency is high in terms of profit balance of carbon dioxide.

Secondly, required size of site is small because of very high speed of fixation of carbon dioxide as compared to green plants. According to results from study conducted at Tokyo Electric Power Research Institute, it is revealed that the speed of fixation of carbon dioxide of microalgae is more than 8 times higher than that of macroalgae and more than 16 times higher than that of pine trees, the most common tree in Korea.

Besides, there is an advantage in that processes for separating and concentrating carbon dioxide are not required due to direct fixation of carbon dioxide from combustion gas. Moreover, microalgae, generated from carbon dioxide fixation, contain numerous useful materials, thereby being utilized for manufacture of expensive bioproducts.

However, if the carbon dioxide fixation process using microalgae is conducted by bioreactors applied to industries, it takes too much electric energy. Thus, it is not easy to supply light energy which is necessarily required for energy saving and microalgae growth.

To solve a problem, Korean Patent Registration no. 10-1072844 (DEVICE FOR CULTIVATING MICROALGAE BY USING EMITTED GAS FROM POWER PLANT) was filed and published.

As illustrated in FIG. 1, the device for cultivating microalgae by using emitted gas from power plant includes a cultivation area (10), an exhaust gas supply area (20) and a microalgae extraction area (30).

The cultivation area (10) consists of a photosynthesis reactor (11) for cultivating microalgae, which is microbial, and a light emitting member (13) for shining light on the photosynthesis reactor (11). Installed to the inside of a greenhouse for maintaining optimal temperature, the cultivation area (10) is provided with exhaust gas from a power plant (1) through the exhaust gas supply area (20).

Specifically, the photosynthesis reactor (11) has a plurality of exhaust gas supply lines (15) for effectively supplying exhaust gas, coming from the exhaust gas supply area (20), and a shut-off valve (15a) in each exhaust gas supply line (15). Also, the photosynthesis reactor (11) has a drain line (17) for emitting microalgae, which stays inside, and a water supply line (19) for adding water toward the inside.

The photosynthesis reactor (11) not only balances cultivation environment of microalgae by means of carbon dioxide ($CO_2$) and heat in exhaust gas, but increases the amount of cultivated microalgae.

The light emitting member (13) is used for stimulating cultivation of microalgae at night or a cloudy day.

The exhaust gas supply area (20) connects the power plant (1) and the cultivation area (10) for supplying exhaust gas, generated from the power plant (1), to the cultivation area (10).

The exhaust gas supply area (20) consists of a vent fan (21), a filter member (23) and a heat exchanging area (25).

Connected to a vent line (3) of the power plant (1), the vent fan (21) compulsorily draws in part of exhaust gas emitted to a stack (5) throughout the vent line (3) and then, delivers to the photosynthesis reactor (11).

The filter member (23) eliminates foreign substances contained in exhaust gas which is discharged by the vent fan (21).

The heat exchanging area (25) performs heat exchange of exhaust gas to reduce temperature of exhaust gas which passes through the filter member (23).

Property reduced temperature in the heat exchanging area (25), exhaust gas is supplied to the photosynthesis reactor (11) throughout a supply line (15), thereby making carbon dioxide eliminated.

The microalgae extraction area (30) is comprised of a drainage pump (31), installed in the drain line (17) of the photosynthesis reactor (11); a storage tank (33) for storing water discharged from the drain line (17); and a separation member (35) for separating water and microalgae.

The drainage pump (31) compulsorily discharges microalgae, cultivated in the photosynthesis reactor (11), to the storage tank (33). When microalgae is compulsorily discharged by the drainage pump (31), water in the photosynthesis reactor (11) is discharged together.

The storage tank (33) is connected to the separation member (35), and water, contained inside, is supplied to the separation member (35).

The separation member (35) consists of a centrifuge (35a) for separating water and microalgae by means of turning force and water of the storage tank (35); and a storage tank (35b) for storing water, discharged from the centrifuge (35a).

There are a plurality of centrifuges (35a) for optimizing efficiency in microalgae separation, and water, coming from microalgae separation, is discharged to the storage tank (35b). Although two centrifuges (35a) are illustrated in the present embodiment, the number of centrifuges (35a) may be one or more than three in accordance with a need of a user.

Discharged to the storage tank (35b) and fed to the heat exchanging area (25) by means of a drain water supply area (40), water is used as a medium of heat exchange of the heat exchanging area (25).

The drain water supply area (40) comprises a connection line (41) for connecting the storage tank (35b) and the heat exchanging area (25) in order to transfer water of the storage tank (35b) to the heat exchanging area (25); and a feed pump (43) installed on the connection line (41).

However, the traditional device for cultivating microalgae by using emitted gas from power plant includes the vent fan in the vent line. Thus, emitted gas is not actively supplied by differential gas pressure, and the photosynthesis reactor of the cultivation area is damaged by pressure or water is overflowed because of pulsatory supply.

In addition, in the traditional device for cultivating microalgae by using emitted gas from power plant, moisture in emitted gas makes the vent line full of water. Thus, it causes breakdown of the vent fan and gives a bad influence on microalgae growth due to water inflow into a photosynthesis cultivator.

PRIOR ART

Reference

Korean Patent Registration No. 10-1072844

DISCLOSURE

Technical Problem

For solving above problems, the object of the present invention is to provide an extracting device supplying fixed quantity of exhaust gas for industrial facility which supplies a certain amount of exhaust gas by installing a gas supply pipe, in which two blowers are arranged in a line, at a stack and operating each blower in accordance with a predetermined input value.

Further, the other object of the present invention is to provide the extracting device supplying fixed quantity of exhaust gas for industrial facility which blocks water inflow into sources by installing the gas supply pipe vertically to a stack, condensing moisture in exhaust gas at the end of the gas supply pipe, installing a valve for discharging condensed water toward the outside, supplying exhaust gas to a blower with a branch gas pipe at a higher position than a level of condensed water of the gas supply pipe, and installing a trap to a connection pipe, which is extended for supplying exhaust gas, coming from the blower, to demanders.

Technical Solution

To accomplish above objects, the present invention comprises: a first gas supply pipe configured to extract part of exhaust gas from a stack and to form a first horizontal area, installed on top for horizontally penetrating into the side of the stack, a vertical area, vertically bent from the first horizontal area in the direction of ground, and a second horizontal area, horizontally located from the vertical area; a first branch gas supply pipe configured to be installed at the bottom side of the vertical area of the first gas supply pipe; a second branch gas supply pipe configured to be connected in parallel to the first branch gas supply pipe at the bottom side of the vertical area of the first gas supply pipe; a second gas supply pipe configured to supply exhaust gas, coming from the first branch gas supply pipe and the second branch gas supply pipe, to sources; a first blower configured to be operated in accordance with external power control at the first branch gas supply pipe; a second blower configured to be operated in accordance with external power control at the second branch gas supply pipe; a first pressure gauge configured to be installed on the first branch gas supply pipe and output a contact signal if the measured internal pressure of the pipe is out of a predetermined range of a first reference pressure value; a second pressure gauge configured to be installed on the second branch gas supply pipe and output a contact signal if the measured internal pressure of the pipe is out of a predetermined range of a second reference pressure value; and a switching element configured to supply the first and second blowers to power in accordance with the contact signal, outputted from the first and second pressure gauges.

Hereinafter, the extracting device supplying fixed quantity of exhaust gas for industrial facility further comprises an inverter which soft starts the first and second blowers.

Hereinafter, the first horizontal area of the first gas supply pipe includes a main valve for supplying and blocking exhaust gas.

Hereinafter, the first horizontal area of the first gas supply pipe is located to the side of the stack while keeping a certain distance from the ground for the purpose of supplying homogenous exhaust gas.

Hereinafter, the first gas supply pipe includes a solenoid valve for automatically discharging condensed water from the end of the second horizontal area toward the outside.

Hereinafter, the second gas supply pipe includes a trap for discharging condensed water toward the outside.

Hereinafter, the contact signal of the first pressure gauge outputs a contact signal which turns off the switching element if the pressure is over the predetermined range of the first reference pressure value, and outputs a contact signal which turns on the switching element if the pressure is less than the predetermined range of the first reference pressure value.

Hereinafter, the contact signal of the second pressure gauge outputs a contact signal which turns off the switching element if the pressure is over the predetermined range of the second reference pressure value, and outputs a contact signal which turns on the switching element if the pressure is less than the predetermined range of the second reference pressure value.

Hereinafter, the second pressure gauge sets up the range of the second reference pressure value in the range of the first reference pressure value of the first pressure gauge.

Advantageous Effects

According to the extracting device supplying fixed quantity of exhaust gas for industrial facility of the present invention, as constituted above, it enables to supply a certain amount of exhaust gas by installing a gas supply pipe, in which two blowers are arranged in a line, at a stack and operating each blower in accordance with a predetermined input value.

Further, according to the present invention, it enables to block water inflow into sources by installing the gas supply pipe vertically to a stack, condensing moisture in exhaust gas at the end of the gas supply pipe, installing a valve for discharging condensed water toward the outside, supplying exhaust gas to a blower with a branch gas pipe at a higher position than a level of condensed water of the gas supply pipe, and installing a trap to a connection pipe, which is extended for supplying exhaust gas, coming from the blower, to demanders.

DESCRIPTION OF THE PREFERRED EMBODIMENTS

The configuration of an extracting device supplying fixed quantity of exhaust gas for industrial facility, according to the present invention, will be described in detail with the accompanying drawing.

In the following description of the present invention, a detailed description of known incorporated functions and configurations will be omitted when to include them would make the subject matter of the present invention rather unclear. Also, the terms used in the following description are defined taking into consideration the functions provided in the present invention. The definitions of these terms should be determined based on the whole content of this specification, because they may be changed in accordance with the option of a user or operator or a usual practice.

Figure 1:
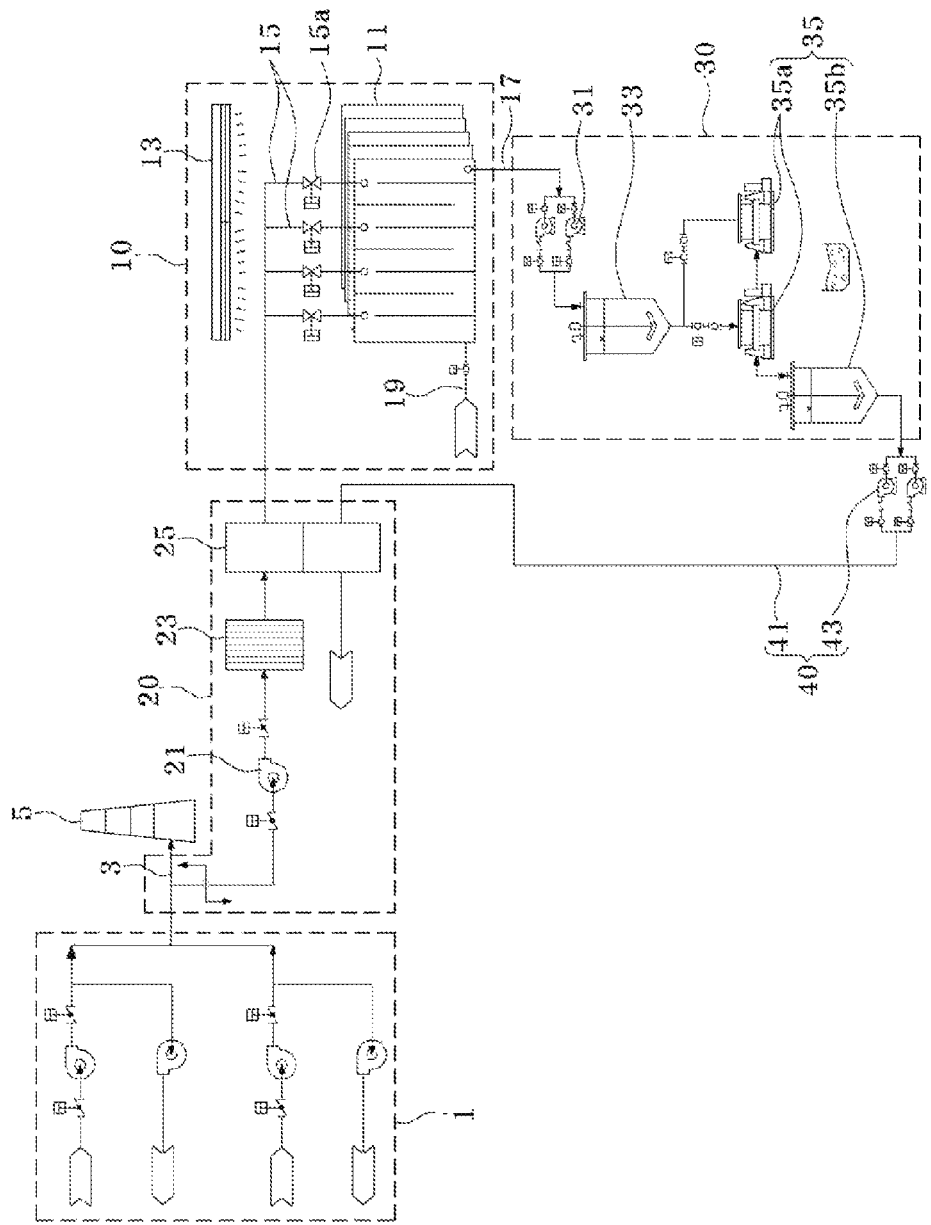
FIG. 1 illustrates a diagram showing the configuration of a conventional device for cultivating microalgae by using emitted gas from power plant.
Figure 2:
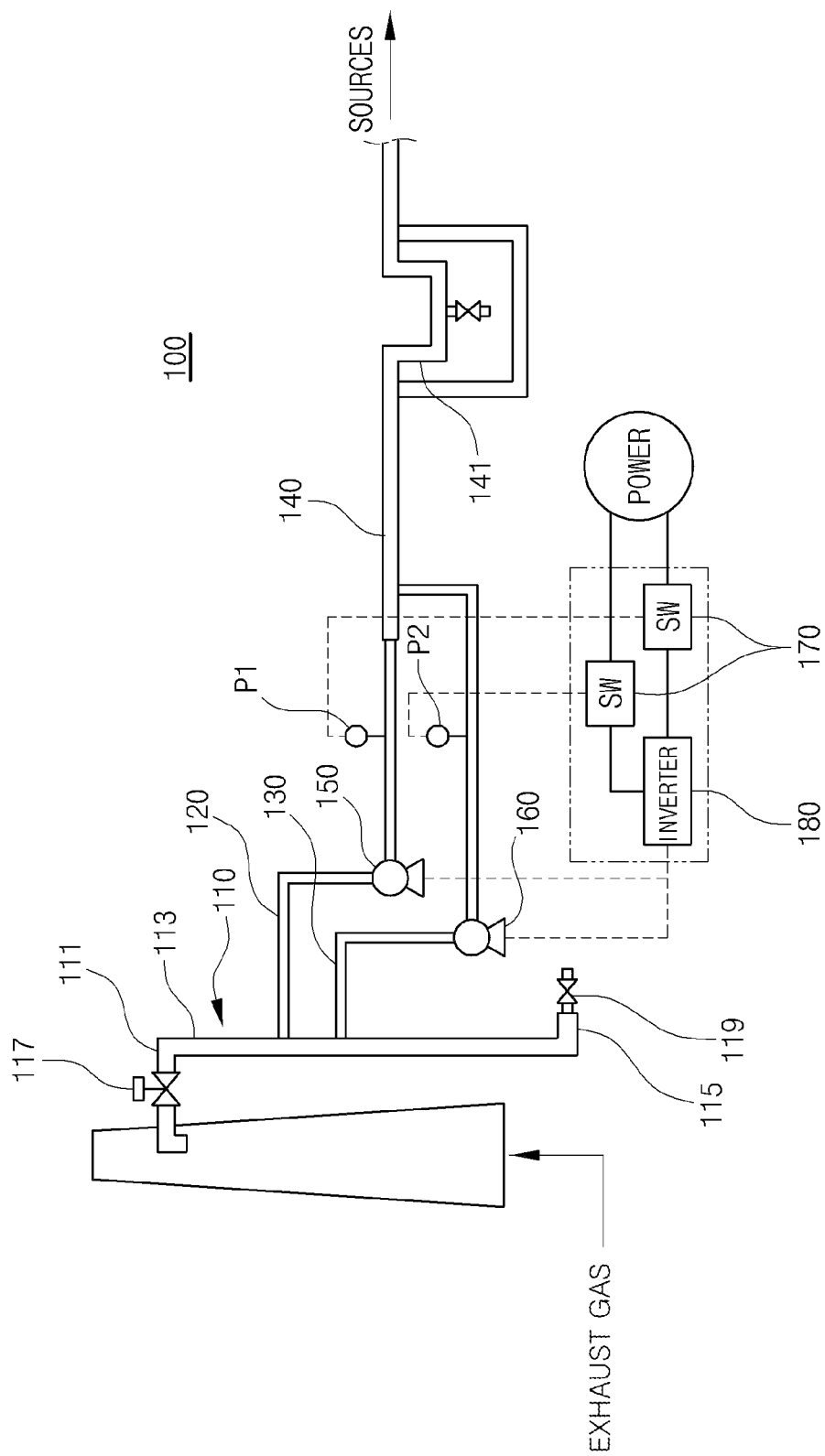
FIG. 2 illustrates a schematic diagram showing the configuration of an extracting device supplying fixed quantity of exhaust gas for industrial facility according to the present invention.

FIG. 2 illustrates a schematic diagram showing the configuration of an extracting device supplying fixed quantity of exhaust gas for industrial facility according to the present invention.

Referring to FIG. 2, an extracting device supplying fixed quantity of exhaust gas for industrial facility (100) according to the present invention comprises a first gas supply pipe (110), a first branch gas supply pipe (120), a second branch gas supply pipe (130), a second gas supply pipe (140), a first blower (150), a second blower (160), a first pressure gauge (P1), a second pressure gauge (P2), and a switching element (170).

First, extracting part of exhaust gas from a stack, the first gas supply pipe (110) comprises a first horizontal area (111) formed on top for horizontally penetrating into the side of a stack; a vertical area (113) vertically bent from the first horizontal area (111) in the direction of ground; and a second horizontal area (115) horizontally formed from the vertical area (113). Hereinafter, the first horizontal area (111) of the first gas supply pipe (110) includes a main valve (117) for supplying and blocking exhaust gas, and is installed to the side of the stack while keeping a certain distance (e.g., 30M as for 80M stack) from the ground for the purpose of supplying homogenous exhaust gas. Hereinafter, the first gas supply pipe (110) comprises a solenoid valve (119) for automatically discharging condensed water from the end of the second horizontal area (115) toward the outside.

In addition, the first branch gas supply pipe (120) is installed on the bottom side of the vertical area (113) of the first gas supply pipe (110). At this time, it is desirable that a diameter of the first branch gas supply pipe (120) is smaller than that of the first gas supply pipe (110).

In addition, the second branch gas supply pipe (130) is connected in parallel to the first branch gas supply pipe (120) at the bottom side of the vertical area of the first gas supply pipe (110). At this time, it is desirable that a diameter of the second branch gas supply pipe (130) is smaller than that of the first gas supply pipe (110).

Further, the second gas supply pipe (140) supplies exhaust gas, coming from each of the first branch gas supply pipe (120) and the second branch gas supply pipe (130), to sources such as a microalgae cultivator and an absorption tower. Hereinafter, the second gas supply pipe (140) includes a trap (141) for discharging condensed water, which comes from gas supply, toward the outside.

Continuously, installed on the first branch gas supply pipe (120), the first blower (150) is operated in accordance with power control of a switching element (170), as explained below, and is fed with exhaust gas of the first gas supply pipe through the first branch gas supply pipe (120) to the second gas supply pipe (140).

Next, installed on the second branch gas supply pipe (130), the second blower (160) is operated in accordance with power control of the switching element (170), and is fed with exhaust gas of the first gas supply pipe through the second branch gas supply pipe (130) to the second gas supply pipe (140).

Further, installed on the first branch gas supply pipe (120), the first pressure gauge (P1) measures internal pressure of the pipe and outputs a contact signal if the pressure is over or less than the predetermined range of a first reference pressure value. Hereinafter, if the pressure is over the predetermined range of the first reference pressure value, the first pressure gauge (P1) outputs a contact signal which turns off the switching element (170), and if the pressure is less than the predetermined range of the first reference pressure value, the first pressure gauge (P1) outputs a contact signal which turns on the switching element (170).

Furthermore, installed on the second branch gas supply pipe (130), the second pressure gauge (P2) measures internal pressure of the pipe and outputs a contact signal if the pressure is over or less than the predetermined range of a second reference pressure value. Hereinafter, if the pressure is over the predetermined range of the second reference pressure value, the second pressure gauge (P2) outputs a contact signal which turns off the switching element (170), and if the pressure is less than the predetermined range of the second reference pressure value, the second pressure gauge (P2) outputs a contact signal which turns on the switching element (170). Here, it is desirable that the second pressure gauge (P2) has a fast supply period with the second reference pressure value, which is set up in the range of the first reference pressure value of the first pressure gauge (P1), for preventing generation of differential pressure or pulsation in case of exhaust gas supply to the second gas supply pipe (140). For instance, if the range of the first reference pressure value is 0.15-0.3 kgf/cm$^2$, the range of the second reference pressure value is set to 0.15-0.3 kgf/cm$^2$.

In addition, the switching element (170), as relay, is respectively installed at the first pressure gauge (P1) and the second pressure gauge (P2), thereby supplying or blocking power to the first blower (150) and the second blower (160).

Meanwhile, the extracting device supplying fixed quantity of exhaust gas for industrial facility according to the present invention further includes an inverter (180) for preventing damage, resulting from rapid start-up, by soft starting the first blower (150) and the second blower (160).

Hereinafter, the extracting device supplying fixed quantity of exhaust gas for industrial facility according to the present invention will be described in detail with the accompanying drawing.

First, if the main valve (170) is open, exhaust gas in a stack (101) is flowed into the first gas supply pipe (110).

In this condition, the first branch gas supply pipe (120) and the second branch gas supply pipe (130) do not have exhaust gas and their pressure is less than the range of the first and second reference pressure values. Thus, a signal is outputted from the first pressure gauge (P1) and the second pressure gauge (P2) for turning on the switching element (170).

Then, power is supplied to the first blower (150) and the second blower (160) with the switching element (170), which is operating.

Accordingly, flowing into the first branch gas supply pipe (120) and the second branch gas supply pipe (130), exhaust gas is supplied to sources such as microalgae cultivators, absorption towers throughout the second gas supply pipe (140).

In this condition, if pressure, measured in the first pressure gauge (P1) or the second pressure gauge (P2), is over the predetermined range of the first and second reference pressure value, the first pressure gauge (P1) or the second pressure gauge (P2) turns off the switching element (170), thereby blocking power supply to the first blower (150) or the second blower (160).

Continuously, exhaust gas is supplied to the second gas supply pipe (140) by repeatedly measuring pressure of the first pressure gauge (P1) or the second pressure gauge (P2).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention is available in facilities for cultivating microalgae by means of exhaust gas, facilities for absorbing carbon dioxide in exhaust gas, etc.

EXPLANATIONS OF NUMERAL REFERENCE 110, 140: first and second gas supply pipes
120, 130: first and second branch supply pipes
150, 160: first and second blowers
170: a switching element
180: an inverter
P1, P2: first and second pressure gauges

The invention claimed is:

1. An extracting apparatus for supplying a fixed quantity of exhaust gas for industrial facility, the apparatus comprising:
    a first gas supply pipe configured to extract part of exhaust gas from a stack and including a first horizontal area located on top thereof and horizontally penetrating into a side of the stack, a vertical area vertically bent from the first horizontal area in a direction of ground, and a second horizontal area horizontally extending from the vertical area;
    a first branch gas supply pipe configured to be installed at a bottom side of the vertical area of the first gas supply pipe;
    a second branch gas supply pipe configured to be connected in parallel to the first branch gas supply pipe at the bottom side of the vertical area of the first gas supply pipe;
    a second gas supply pipe configured to supply exhaust gas coming from the first branch gas supply pipe and the second branch gas supply pipe to sources;
    a first blower configured to be operated in accordance with external power control at the first branch gas supply pipe;
    a second blower configured to be operated in accordance with the external power control at the second branch gas supply pipe;
    a first pressure gauge configured to be installed on the first branch gas supply pipe and output a contact signal if a measured internal pressure of the first branch gas supply pipe is out of a predetermined range of a first reference pressure value;
    a second pressure gauge configured to be installed on the second branch gas supply pipe and output a contact signal if a measured internal pressure of the second branch gas supply pipe is out of a predetermined range of a second reference pressure value; and
    a switching element configured to supply power to the first and second blowers in accordance with the contact signal outputted from the first and second pressure gauges.

2. The apparatus according to claim 1, further comprising an inverter configured to start the first and second blowers.

3. The apparatus according to claim 1, wherein the first horizontal area of the first gas supply pipe includes a main valve for supplying and blocking exhaust gas.

4. The apparatus according to claim 1, wherein the first horizontal area of the first gas supply pipe is connected to the side of the stack while keeping a certain distance from the ground for supplying homogenous exhaust gas.

5. The apparatus according to claim 1, wherein the first gas supply pipe includes a solenoid valve for automatically discharging condensed water from an end of the second horizontal area toward the outside.

6. The apparatus according to claim 1, wherein the second gas supply pipe includes a trap for discharging condensed water toward the outside.

7. The apparatus according to claim 1, wherein the contact signal of the first pressure gauge turns off the switching element if the measured internal pressure of the first branch gas supply pipe is over the predetermined range of the first reference pressure value, and turns on the switching element if the measured internal pressure of the first branch gas supply pipe is less than the predetermined range of the first reference pressure value.

8. The apparatus according to claim 7, wherein the contact signal of the second pressure gauge turns off the switching element if the measured internal pressure of the second branch gas supply pipe is over the predetermined range of the second reference pressure value, and turns on the switching element if the measured internal pressure of the second branch gas supply pipe is less than the predetermined range of the second reference pressure value.

9. The apparatus according to claim 8, wherein the second pressure gauge sets up the range of the second reference pressure value in the range of the first reference pressure value of the first pressure gauge.

* * * * *